US00PP16641P2

(12) United States Plant Patent
Utecht

(10) Patent No.: US PP16,641 P2
(45) Date of Patent: Jun. 13, 2006

(54) ***GERANIUM* PLANT NAMED 'FISTAFIRE'**

(50) Latin Name: *Pelargonium zonale*
Varietal Denomination: Fistafire

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 83 days.

(21) Appl. No.: 10/998,605

(22) Filed: Nov. 30, 2004

(51) Int. Cl.
*A01H 5/00* (2006.01)

(52) U.S. Cl. ..... Plt./327
(58) Field of Classification Search ..... Plt./327, Plt./328
See application file for complete search history.

(56) References Cited
PUBLICATIONS
German PBR Application No. PEL 1899 filed Jun. 4, 2003 (Copy of German Gazettes dated 1) Jul. 15, 2003—Listing Assigned Application for Protection Number (2 pgs), and 2) May 15, 2004—Publishing Proposed Variety Denomination (2 pgs)).
Canadian PBR Application No. 03–3905 filed Nov. 21, 2003 (Copy of Canadian Plant Varieties Journal dated Jan., 2004 Listing Assigned Application Number (2 pgs).

*Primary Examiner*—Kent Bell
(74) *Attorney, Agent, or Firm*—Foley & Lardner, LLP

(57) ABSTRACT

A new and distinct cultivar of *geranium* plant named 'Fistafire' particularly characterized by the combined features of large-size orange-red, semi-double flowers; large inflorescences on long, reddish peduncles; large leaves with dark green foliage and narrow but strong zonation; over medium sized plant habit, with a good proportion between the foliage canopy and the height of the inflorescences; and early to mid spring flowering response.

1 Drawing Sheet

Genus and species of the plant claimed: *Pelargonium zonale* L'Héritier (hybrid).
Variety denomination: 'Fistafire'.

BACKGROUND OF THE INVENTION

The present invention comprises a new and distinct cultivar of *geranium*, botanically known as *Pelargonium zonale,* and hereinafter referred to by the cultivar name 'Fistafire'.

'Fistafire' is a product of a planned breeding program which had the objective of creating new zonal *geranium* cultivars with red flower color, dark-green, zoned foliage, and about medium sized plant habit.

'Fistafire' originated from a hybridization made by the inventor, Angelika Utecht, in a controlled breeding program in Hillscheid, Germany, in 1998. The female parent was the patented variety 'Fishelen' (U.S. Plant Pat. No. 12,727), characterized as having salmon-pink, semi-double flowers, medium green foliage with relatively strong zonation, and medium growth habit. The male parent of 'Fistafire' was a tetraploid line of the unpatented commercial variety 'Stadt Bern', which was characterized by orange-red, single-type flowers with narrow petals, red peduncles, dark green, zoned foliage and vigorous growth habit.

'Fistafire' was selected as one flowering plant within the progeny of the stated cross by Angelika Utecht in 1999 in a controlled environment in Moncarapacho, Portugal.

The first act of asexual reproduction of 'Fistafire' was accomplished when vegetative cuttings were taken from the initial selection in the fall of 1999 in a controlled environment in Moncarapacho, Portugal, by, or under the supervision of, Angelika Utecht.

Horticultural examination of plants grown from cuttings of the plant initiated in May of 2000, in Hillscheid, Germany, and continuing thereafter, has demonstrated that the combination of characteristics as herein disclosed for 'Fistafire' are firmly fixed and are retained through successive generations of asexual reproduction.

BRIEF SUMMARY OF THE INVENTION

'Fistafire' has not been observed under all possible environmental conditions. The phenotype may vary significantly with variations in environment such as temperature, light intensity and day length. The following observations, measurements, and comparisons describe plants grown in Hillscheid, Germany, under greenhouse conditions which approximate those generally used in commercial practice.

The following traits have been repeatedly observed and are determined to be basic characteristics of 'Fistafire' in combination distinguish this *geranium* as a new and distinct cultivar:

1. large-sized, orange-red, semi-double flowers;
2. relatively large inflorescences, reddish peduncles;
3. large leaves, very dark-green with narrow, but relatively strong zonation;
4. attractive contrast between the flower color and the very dark foliage;
5. medium or over sized plant habit; and
6. early to mid spring flowering response.

Of the many commercial cultivars known to the present inventor, the most similar in comparison to 'Fistafire' are the varieties 'Tango' (U.S. Plant Pat. No. 5,933), and the co-pending variety 'Fishimred' (U.S. Plant patent application Ser. No. 10/998,559).

In comparison to 'Tango', 'Fistafire' has a lighter and more orange-red hue of flowers, and even darker green foliage with distinct zonation, while leaves of 'Tango' show practically no zonation. Furthermore, 'Fistafire' grows somewhat taller than 'Tango'.

In comparison to 'Fishimred', 'Fistafire' has darker green foliage with stronger zonation, and, due to a less vigorous growth habit, are somewhat smaller sized plants.

BRIEF DESCRIPTION OF THE DRAWING

The accompanying photographic drawing shows typical flower and foliage characteristics of 'Fistafire' with colors being as true as possible with an illustration of this type. The photographic drawing shows a side perspective view of a flowering potted plant of 'Fistafire' with leaves, buds and inflorescences.

DETAILED BOTANICAL DESCRIPTION

The measurements were taken in Hillscheid, Germany, in mid May, 11 weeks after planting of rooted cuttings. The plants were growing in 14 cm pots, they had not been pinched.

In the following description, color references are made to The Royal Horticultural Society Color Chart. The color values were determined indoors from plants growing in a green-house in May 2003 in Hillscheid, Germany.

Parentage:

*Male parent.*—Tetraploid line of unpatented commercial variety, 'Stadt Bern'.

*Female parent.*—'Fishelen' (U.S. Plant Pat. No. 12,727).

Classification: *Pelargonium zonale* L'Héritier (hybrid).

Propagation: Vegetative cuttings.

Inflorescence:

*Umbel.*—Shape: Between semi-spherical and umbrella-shape. Average diameter: 116 mm. Average depth: 55 mm. Number of flowers per umbel: About 30–40.

*Peduncle.*—Peduncle length: 114 mm. Peduncle diameter: 5 mm. Peduncle color: Mainly deep greyish-purple, RHS 184 A.

*Pedicel.*—Pedicel length: 36 mm in length. Pedicel diameter: 2 mm or less. Pedicel color: Greyish-red, RHS 181 B.

*Corolla.*—Average diameter: 55 mm. Depth: About 15 mm. Form: Semi-double-type. Shape: Almost round outline, though often with a gap between upper and lower petals.

*Petaloids.*—Number of petaloids: 2–3. Length: 5–15 mm. Width: 3–10 mm. Overall shape: Variable, often spatulate to narrow obovate, often wavy or curved. Apex shape: Acute or rounded. Base shape: Acute. Margin: Entire. Color of upper petaloids: Orange-red, RHS N 30 A. Color of lower petaloids: Orange-red, RHS N 30 A.

*Petals.*—Number of petals: 6–8. Shape of petals: Obovate, base acute, upper end is truncate or rounded, margin is entire or very slightly crenated at the tips. Size of petals: Upper petals: 30–32 mm long, 26–30 mm wide; lower petals: 28–30 mm long, 25–27 mm wide. Color (general tonality from a distance of three meters): Deep orange-red. Color of upper petals: Orange-red, RHS N30 A. Markings of upper petals: No distinct markings. Color of lower petals: Orange-red, RHS N30 A. Markings of lower petals: None. Color of lower surface of petals: Mainly red, RHS 40 B.

*Sepals.*—Color of sepals: Outer surface: mainly greyish-red, RHS 181 A, with greenish tips, RHS 143 A. Inner surface: mainly yellow-green, RHS 144 B. Number of sepals: 5. Shape of sepals: Linear to lanceolate, acute tip, fused base, surface with very short pubescence, margin entire. Size of sepals: 11 mm long, 4–5 mm wide for the largest upper sepal, 2–3 mm in width for the other sepals.

*Bud (just prior to petals unfolding).*—Shape: Elliptical. Color of sepals: Yellow-green, RHS 143 C. Color of petals: Red, RHS 38 C to 41 C, marbeled. Length: 13–14 mm. Width: 8 mm.

Reproductive organs:

*Androecium.*—2–5 fertile anthers, moderate pollen, orange-red, RHS 30 A, filaments white, RHS 155 D, to light-pink, RHS 52 D.

*Gynoecium.*—One pistil, whitish style, RHS 155 D to red-purple, 65 D, stigma 5–6-lobed stigma, orange-red, RHS N30 A.

*Fertility/seed set.*—Few, mainly from late summer to fall.

*Fruit.*—Oblong, about 5–6 mm wide, rostrum (beak) 38–42 mm long.

*Seed.*—Oblong, 4–5 mm long, brown (greyed-orange), RHS 177 B.

*Spring flowering response period.*—In Hillscheid, Germany, in 2003 plants had on average 0.7 flowers opened 8 weeks after planting of rooted cuttings.

*Outdoor flower production.*—Continuously flowering, fair number of flowers for a variety with big inflorescence; the flower count in 2003 in Hillscheid, Germany, indicated about 15–20 inflorescences per plant in late summer.

*Durability.*—Good stability of flower color, no fading, fair rain resistance.

*Lastingness of the individual flower.*—About 7–8 days at 18° C., about 18 days for the umbel.

*Fragrance.*—None.

Plant:

*Foliage.*—Shape: Kidney-shaped to nearly round, with cordate base, with the gap between the lowest lobes almost closed to closed, apex rounded with weak lobes, margin distinctly wavy. Margin: Bicrenate. Texture: Upper surface smooth, slightly glossy. Size of leaf: 110 mm wide, 65 mm long. Color of upper surface: Dark green, near RHS 139 A. Color of zonation: Narrow, but strong in color, dark brown, about RHS 200 B. Color of lower surface: Green, RHS 137 C. Petioles: 70–90 mm long, 3 mm diameter, yellow-green in color, approximately RHS 143 C.

*General appearance and form.*—Stem color: Mainly greyish-purple, RHS 184 B. Internode length: 10–20 mm. Branching pattern: 4.3 branches. Size of plants: Height: 14.1 cm, Spread: 26.1 cm; 11-week-old plants, as described, measured from the top of the soil (base of the main stem) to the surface of the foliage canopy, without inflorescences.

I claim:

1. A new and distinct cultivar of *geranium* plant named 'Fistafire', as described and illustrated herein.

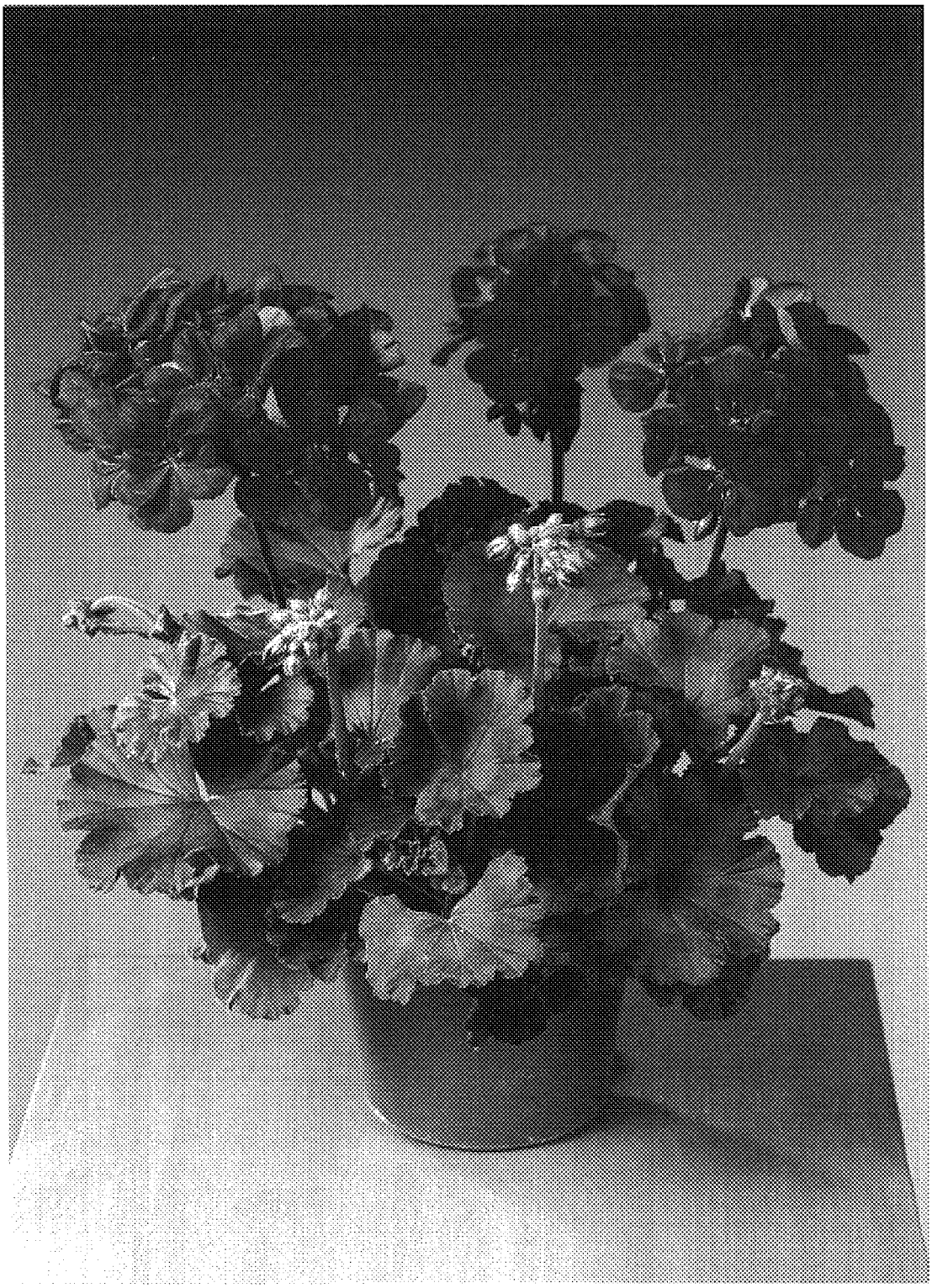

* * * * *